US00PP25755P3

(12) United States Plant Patent
Schoone

(10) Patent No.: US PP25,755 P3
(45) Date of Patent: Jul. 28, 2015

(54) ***PHALAENOPSIS* ORCHID PLANT NAMED 'FLOR169431'**

(50) Latin Name: ***Phalaenopsis* hybrid**
Varietal Denomination: FLOR169431

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 102 days.

(21) Appl. No.: 13/987,999

(22) Filed: Sep. 23, 2013

(65) Prior Publication Data

US 2014/0090126 P1 Mar. 27, 2014

Related U.S. Application Data

(60) Provisional application No. 61/704,952, filed on Sep. 24, 2012.

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'FLOR169431' particularly characterized by flowers which are white with a purple mark in the center; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'FLOR169431'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'FLOR169431'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'FLOR169431' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'FLOR169431' originated from a cross made by the inventor in 2000 in Strengweg, Heemskerk, The Netherlands. The female or seed parent is the *Phalaenopsis* cultivar designated 'Tying Shin Cupid', unpatented. The male or pollen parent is the *Phalaenopsis* cultivar designated 'Free Spirit', unpatented. The new *Phalaenopsis* 'FLOR169431' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture was first performed in July, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'FLOR169431', which in combination distinguish this *Phalaenopsis* as a new and distinct cultivar:

1. flowers which are white with a purple mark in the center;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'FLOR169431', the female parent 'Tying Shin Cupid' has bronze colored flowers with a purple labellum, the male parent 'Free Spirit' has white colored flowers, whereas the flowers of 'FLOR169431' are white with a purple mark in the center and some purple and yellow in the labellum.

Presently, the commercial cultivar to which 'FLOR169431' can be meaningfully compared is the *phalaenopsis* orchid 'Cupid Spirit' (U.S. application Ser. No. 13/998,021). The flowers of 'FLOR169431' have a purple mark in the center, whereas the flowers of 'Cupid Spirit' also have a lot of purple spots.

BRIEF DESCRIPTION OF THE PHOTOGRAPHS

The accompanying photographs illustrate the overall appearance of the new *Phalaenopsis* 'FLOR169431' showing the colors as true as is reasonably possible with colored reproductions of this type. Colors in the photographs may differ slightly from the color values cited in the detailed botanical description, which accurately describe the color of 'FLOR169431'.

DETAILED BOTANICAL DESCRIPTION

Figure 1:
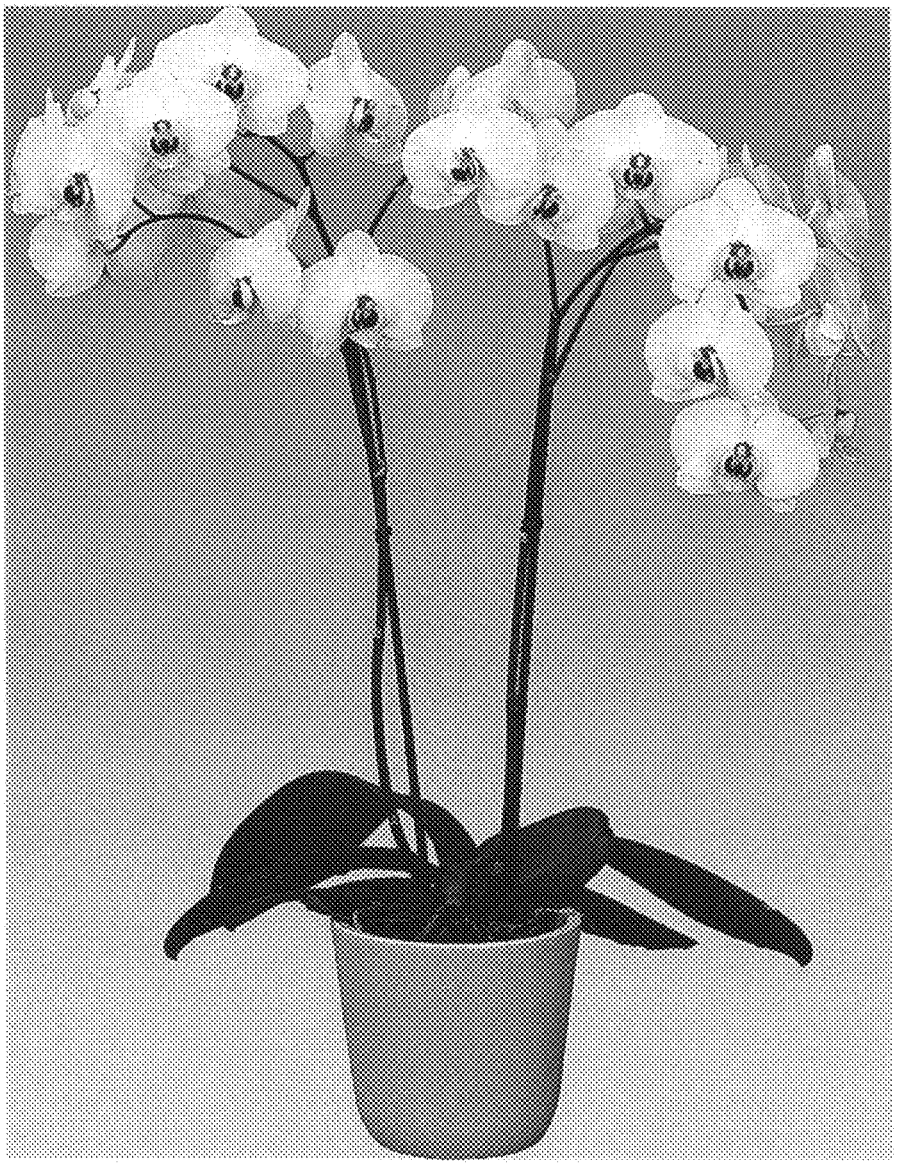
FIG. 1 shows a side view perspective of a typical flowering plant of 'FLOR169431' in a 12 cm pot, at 16 months of age.

The new *Phalaenopsis* cultivar 'FLOR169431' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'FLOR169431' as grown in a greenhouse in Strengweg, Heemskerk, The Netherlands, under conditions which closely approximate those generally used in commercial practice. Initially, the ideal temperature to grow plants of 'FLOR169431' is 27° C. during the day and at night. Then, during the flowering phase of 'FLOR169431', the ideal growing temperature is 20-22° C. during the day and 18° C. at night. Light levels for growing 'FLOR169431' are a minimum of 5,000 lux and a maximum of 10,000 lux. A balanced fertilizer with level of 200 ppm N, 87 ppm P, 168 ppm K is applied. Duration of growth of 'FLOR169431' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'FLOR169431' plants described is 12 months after potting.

Classification:

*Botanical.*—*Phalaenopsis* hybrid.

Parentage:

*Female or seed parent.*—*Phalaenopsis* cultivar designated 'Tying Shin Cupid', unpatented.

*Male or pollen parent.*—*Phalaenopsis* cultivar designated 'Free Spirit', unpatented.

Propagation:

*Type.*—Tissue culture.

*Rooting habit and description.*—Approximately 3 mm-6 mm wide and grey/green (RHS 193C) in color; freely branching. It takes 12 weeks for plants growing in tissue culture to initiate roots.

Plant:

*Size at maturity.*—Height: about 65 to 75 cm. Spread: about 45 to 65 cm.

*Growth habit.*—Standard; green (RHS N137C) leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 5 to 8 leaves are produced before flowering.

*Arrangement and attachment.*—Half up/horizontal and on two sides.

*Overall shape of leaf.*—Oval, the tip is blunt and asymmetric.

*Texture.*—Smooth and leathery.

*Pubescence.*—None.

*Mature leaf length.*—About 17 to 29 cm.

*Mature leaf width.*—About 7 to 9 cm.

*Mature leaf thickness.*—About 2 mm.

*Mature leaf color.*—Upper side: green (RHS N137C). Under side: green (RHS 138B).

*Leaf base.*—Acute.

*Margin.*—Entire.

*Venation.*—Pattern: parallel. Color of midvein: upper side: green (RHS N137C). Under side: green (RHS 138B).

Raceme:

*Quantity per plant.*—About 1 to 2.

*Number of flowers per raceme.*—About 5 to 18.

*Length.*—About 60 to 70 cm.

*Diameter.*—About 5 mm.

*Strength.*—Strong.

*Aspect.*—Upright.

*Texture.*—Glabrous and smooth.

*Color.*—Green (RHS 143A and RHS 143B).

*Internode.*—Length: about 30 to 40 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 to 20 mm. Diameter (at midpoint): about 15 to 20 mm. Shape: oval/egg-shaped. Color: yellow/green (RHS 145D and RHS 145B) with a purple haze (RHS 77C).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
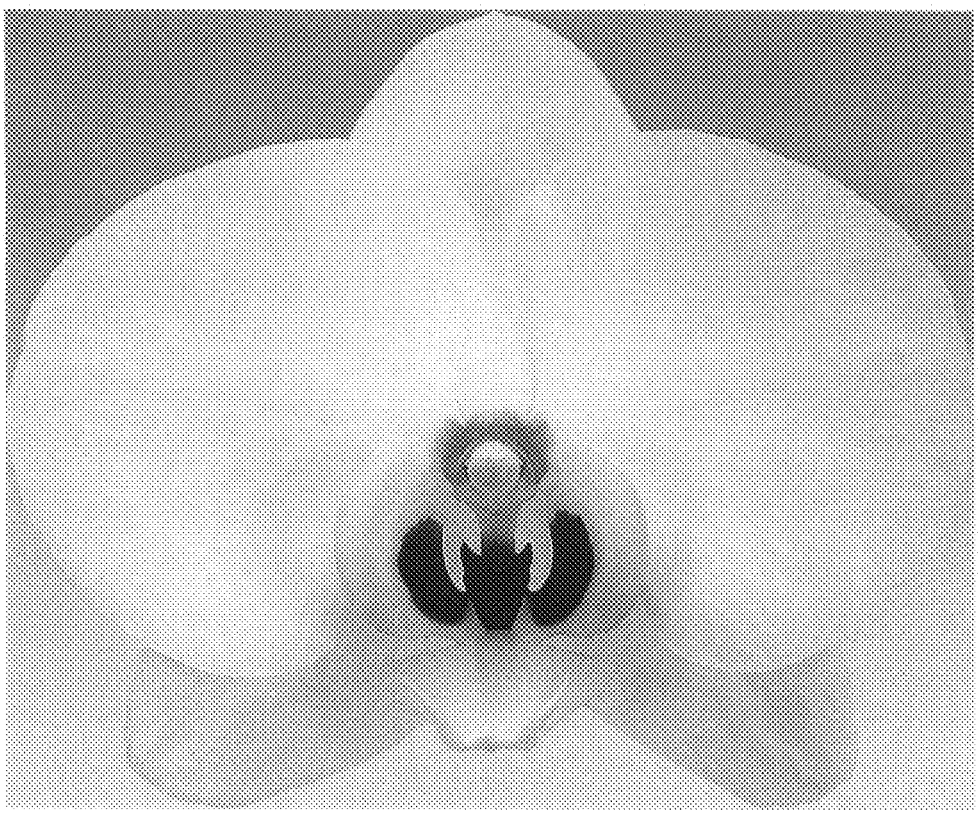
FIG. 2 shows a close-up view of a typical flower of 'FLOR169431'.
Figure 3:
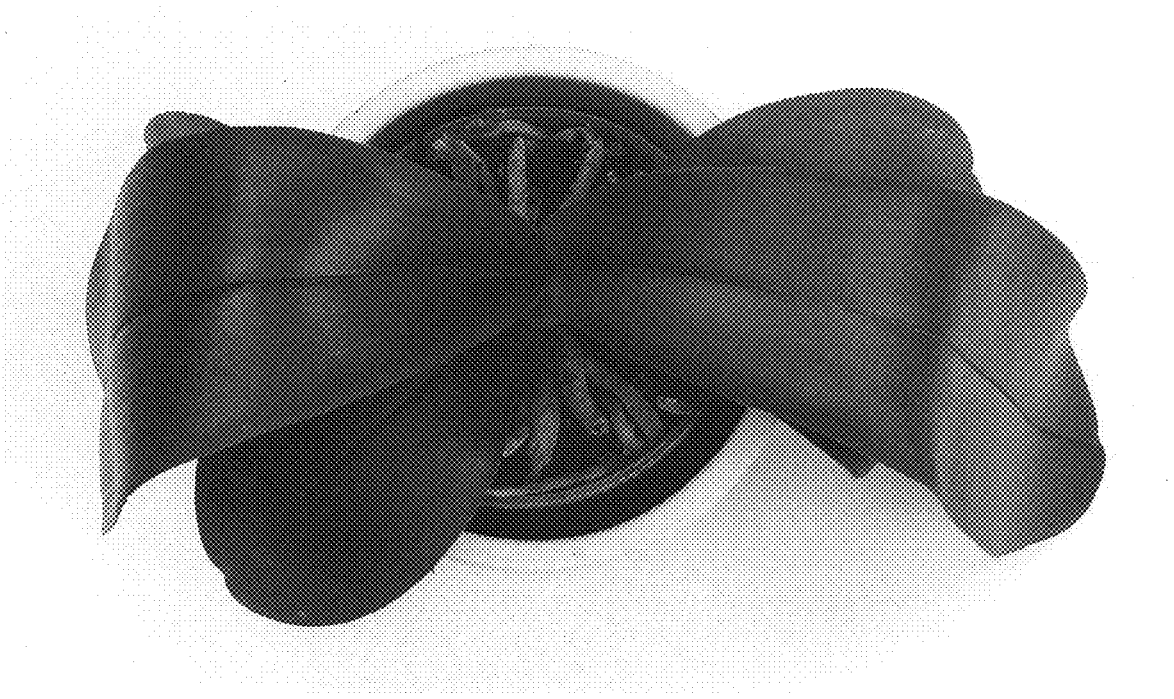
FIG. 3 shows a close-up view of the typical leaves of 'FLOR169431'.

*Flower*.—Rate of opening: Flowers fully opened about 2 to 3 days after petal and sepal separation. Orientation at opening: slanted upward and outward. Shape: Typical shape of *phalaenopsis* orchid, see FIG. 2. Size: Height: about 50 mm to 80 mm. Diameter: about 60 mm to 90 mm. Depth of tube: about 15 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: round. Margin: entire and weakly undulate. Base: broadly ovate. Length: about 40 mm to 55 mm. Width: about 30 mm to 40 mm. Texture: Upper surface: smooth and satiny. Under surface: smooth and satiny. Color (when fully opened): upper surface: Main color is white (RHS NN155C). At the base a purple mark (RHS 77B and RHS 77A). Some also have one or two small purple spots on the petal (RHS 77A). Under surface: Main color is white (RHS NN155C). At the base some purple (RHS 77B).

*Labellum*.—Overall shape: 3-lobed with 2 prominent callosities at central junction of the lateral lobes and base of the midlobe. Lateral lobes of labellum fold upward about the column; the midlobe extends forward and is terminated by 2 long filiform appendages at the apex. Lateral lobes of the labellum are ovate in shape while the midlobe is triangular with a bump and a rib on it. Margin: entire and weakly undulate. Apex: oval. Length: about 18 mm. Width (not flattened): about 20 mm. Texture: Upper & under surface: smooth and satiny. Color (when fully opened): Midlobe, upper surface: Main color is white (RHS NN155C). Corners and a line in the center are yellow (some flowers RHS 12A and some RHS 4A). Some also have some greyed/purple (RHS 187B) spots on the edges of the yellow corners. Under surface: white (RHS NN155C) with yellow in the corners (RHS 12A or RHS 4A) and some have greyed/purple spots (RHS 187B). Lateral lobes: upper surface: main color is white (RHS NN155C). From base, lower edge is yellow (RHS 4A or RHS 12A). From base large greyed/purple mark (RHS 187B and RHS 187C). Under surface: white (RHS NN155C) with yellow bottom edge (RHS 12A or RHS 4A) and a greyed/purple haze near the base (RHS 187B).

*Cirrhi*.—Long (about 18 mm). Color: white (RHS NN155C) and yellow (RHS 12A or RHS 4A).

*Pestle* (*callosities*).—Length: about 4 mm. Width (not flattened): about 6 mm. Color: Sides are white (RHS NN155C) with a yellow haze on the edges (RHS 4D); edges and inside is greyed/purple (RHS 187A and RHS 187B).

*Sepals*.—Arrangement: Outer whorl of petals comprises 3 sepals. Overall shape: elliptical and weakly cupped. Margin: entire and weakly undulate. Length: about 40 mm. Width: about 30 mm. Apex: oval. Texture: Upper & under surface: smooth and satiny. Color (when fully opened): Dorsal and lateral: upper surface: main color is white (RHS NN155C). At the base a purple mark (RHS 77B and RHS 77A). Some also have one or two small purple spots on the petal (RHS 77A). Under surface: Dorsal: white (RHS NN155C) with a purple haze over the main part of the sepal (RHS 77D). Lateral: white (RHS NN155C) with a purple haze close to the base (RHS 77D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 7 mm. Diameter: about 6 mm. Color: purple (RHS 77A and RHS 77B).

*Pollinia*.—Quantity: Two. Diameter: about 2 mm. Color: yellow/orange (RHS 17B).

*Ovary*.—Length: about 4 mm. Diameter: about 6 mm. Color: white (RHS NN155C) with purple (RHS 77C).

*Pedicel*.—Length: about 30 to 40 mm. Diameter: about 3 mm. Texture: glabrous and smooth. Color: Close to the flower white (RHS NN155C) with a purple haze (RHS 77D) which runs into yellow/green (RHS 146D). At the end a little purple (RHS N79B).

Disease/pest resistance susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'FLOR169431', as illustrated and described herein.

* * * * *